(12) United States Patent
Frick et al.

(10) Patent No.: US 6,733,462 B1
(45) Date of Patent: May 11, 2004

(54) BLOOD PRESSURE MONITOR CALIBRATING DEVICE

(75) Inventors: Gerhard Frick, Feldkirch (AT); Te-Hua Lee, Keelung (TW)

(73) Assignee: Microlife Intellectual Property GmbH, Berneck (CH)

( * ) Notice: Subject to any disclaimer, the term of this patent is extended or adjusted under 35 U.S.C. 154(b) by 65 days.

(21) Appl. No.: 10/110,734

(22) PCT Filed: Nov. 9, 2000

(86) PCT No.: PCT/EP00/11068

§ 371 (c)(1), (2), (4) Date: Apr. 16, 2002

(87) PCT Pub. No.: WO01/35821

PCT Pub. Date: May 25, 2001

(30) Foreign Application Priority Data

Nov. 16, 1999 (EP) .............................................. 99122795

(51) Int. Cl.[7] .................................................. A61B 5/02
(52) U.S. Cl. ........................ 600/503; 600/485; 600/499
(58) Field of Search ................................ 600/485, 499, 600/502, 503; 606/202

(56) References Cited

U.S. PATENT DOCUMENTS

| | | | | |
|---|---|---|---|---|
| 3,847,142 A | * | 11/1974 | Williams et al. | 600/507 |
| 4,718,428 A | * | 1/1988 | Russell | 600/492 |
| 5,485,848 A | * | 1/1996 | Jackson et al. | 600/485 |
| 5,509,423 A | * | 4/1996 | Bryars | 600/503 |
| 6,152,880 A | * | 11/2000 | Okada | 600/490 |
| 6,231,517 B1 | * | 5/2001 | Forstner | 600/485 |
| 6,251,080 B1 | * | 6/2001 | Henkin et al. | 600/490 |
| 6,344,025 B1 | * | 2/2002 | Inagaki et al. | 600/490 |
| 6,379,310 B1 | * | 4/2002 | Mori et al. | 600/490 |

FOREIGN PATENT DOCUMENTS

| | | | |
|---|---|---|---|
| EP | 0 342 249 | * | 11/1989 |
| EP | 0 826 334 | * | 3/1998 |

* cited by examiner

Primary Examiner—Michael Peffley
(74) Attorney, Agent, or Firm—Shoemaker and Mattare

(57) ABSTRACT

A wrist type bloodpressure monitor (1) is provided with an interface connector (16) for calibration purposes. The correct values of the blood pressure are measured with a calibration device (20) including an upper arm blood pressure measuring monitor (11). The values (D', S') measured in this way are used to recalibrate the wrist type blood pressure monitor (1). The wrist type blood pressure monitor (1) is therefore provided with an editable memory (5) for the purpose of recalibration.

14 Claims, 2 Drawing Sheets

BLOOD PRESSURE MONITOR CALIBRATING DEVICE

Figure 1:
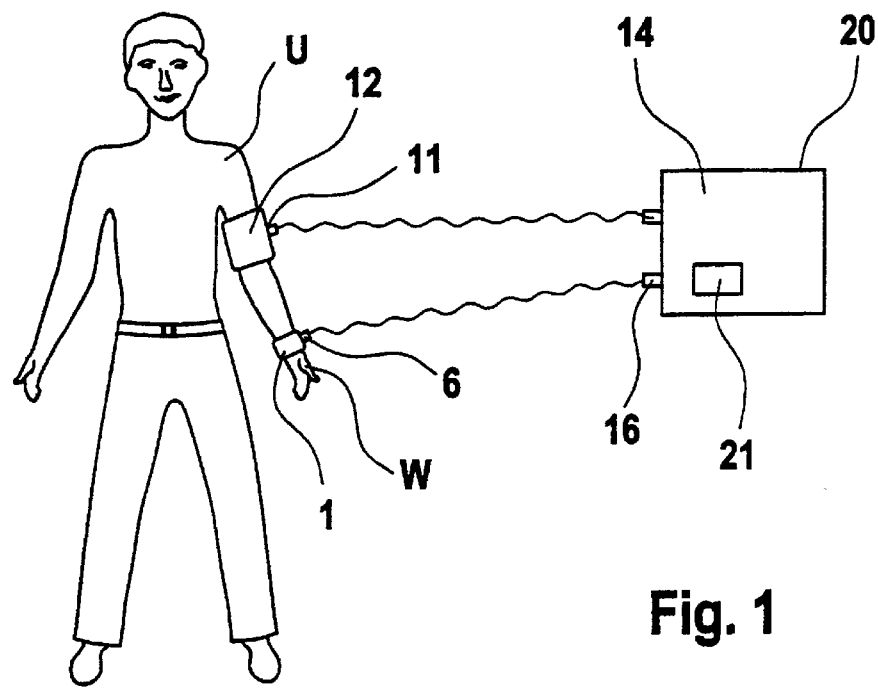

The present invention relates to a blood pressure monitor, a calibrating device and system and a method for calibrating a wrist type blood pressure monitor.

It is well known to use electronic blood pressure monitors for measuring the blood pressure on a patient. Mainly in the field of blood pressure monitors for home it is also known to measure the pressure around the wrist of the patient. This is preferred because of the easier application of the pressure cuff around the wrist as compared to the upper arm.

With regard to the quality of the measurement, wrist type blood pressure monitors are, however, somewhat less favourable. Wrist type blood pressure monitors have always a higher interindividual scattering of the measurement accuracy. This is due to the sensitive and complicate anatomical situation on the human wrist. While in the wrist, there are two arteries, the ulnar and the radial artery, the upper arm comprises just one artery. Measurements on the upper arm are known since a long time and therefore have less uncertainties.

Known blood pressure monitors are calibrated for an anatomical situation which corresponds to an average patient. This calibration may not be adapted to patients having e.g. relatively small or large wrist in the case of wrist type monitors.

It is an object of the present invention to overcome the draw-backs of the prior art, especially to provide a wrist type blood pressure monitor which allows an optimum measurement of the blood pressure on the wrist also for patients who have a different anatomical situation as compared to the average patient. A further object of the invention consists in providing a calibration device for calibrating a wrist type blood pressure monitor. Still a further object of the invention consists in providing a system for calibrating a wrist type blood pressure monitor. An other object of the invention consists in providing a method for calibrating a wrist type blood pressure monitor. The blood pressure monitor shall be simple and economic to manufacture and easily to use and apply.

According to the present invention, these objects are solved with a blood pressure monitor, a calibrating device, a calibration system and a method for calibrating a wrist type blood pressure monitor having the features of the independent patent claims. Calibrating shall mean in the context of the application any adjustment or modification of data stored in a memory in the BPM and used for calculating the blood pressure values.

The blood pressure monitor according to the invention comprises in a known manner an inflatable cuff e.g. adapted to be placed around the wrist of a patient, a pressure sensor for measuring the pressure within the cuff and a calculating arrangement for calculating the blood pressure values based on pressure values measured within the cuff. Such blood pressure monitors are known to those skilled in the art. The blood pressure values, i.e. the systolic and the diastolic blood pressure are determined e.g. with the oscillometric method.

According to the present invention, the calculating arrangement comprises an editable memory for storing data such as calibration data to be used in the calculation process of the blood pressure values within the calculating arrangement. Modifiable data can also be the weight, age or other parameters of the user. In contrast to know blood pressure monitors, where calibration data are pre-set in the factory, the present invention allows to recalibrate the blood pressure monitor by editing the calibration data in the memory. If e.g. a user becomes aware of the fact, that measured values are continuously too high or too low, the blood pressure monitor can be recalibrated. Obviously, the present invention is also useable for calibrating others than wrist type blood pressure monitors, such as finger type monitors or also upper arm monitors, if a reasonable reference site is available.

In a preferred embodiment, the blood pressure monitor comprises an interface connector which is connectable to a calibration device. The calibration device especially may comprise an upper arm type blood pressure monitor. For calibrating the wrist type blood pressure monitor, the blood pressure is measured with the usually more accurate upper arm blood pressure monitor. Other reference measurement sites are also conceivable.

The wrist type blood pressure monitor can be connected to the calibration device via the interface connector. The calibration data on the editable memory can thereafter be adapted in accordance with the blood pressure values measured with the upper arm type blood pressure monitor.

In a further preferred embodiment, the blood pressure monitor comprises a battery compartment for batteries. The interface connector is preferably arranged within this battery compartment. The interface connector therefore is not visible to the user if the battery compartment is closed.

The interface connector is preferably adapted to be connected to an external power supply during calibration. The external power supply can be especially provided by the calibration device. For connecting the interface connector of the wrist type blood pressure monitor to the calibration device, the batteries must be removed first. As soon as the wrist type blood pressure monitor is connected to the calibration device, power for the wrist type blood pressure monitor is supplied by the calibration device.

The editable memory is preferably an EEPROM or a flash-RAM which can be arranged in addition to a memory on the chip of the monitor in which the factory values are stored.

The calibration device for calibrating a wrist type blood pressure monitor according to the present invention comprises a inflatable cuff adapted to be placed around the upper arm of a patient, a pressure sensor for measuring the pressure within the cuff and a calculating arrangement for calculating the blood pressure values based on the pressure measured within the cuff. According to the invention, the calculating arrangement comprises an interface connector connectable with a wrist type blood pressure monitor. Calibration information based on the measurement of the blood pressure made on the upper arm is transferred to the wrist type blood pressure monitor via the interface connector.

The calibrating device preferably comprises a power supply for the wrist type blood pressure monitor during calibration.

A system for calibrating a wrist type blood pressure monitor mainly comprises a calibration device and an upper arm blood measuring monitor. The calibration device is connected or connectable to the wrist type blood pressure monitor. Preferably, the calibration device and the upper arm blood measuring monitor form one unit.

The method for calibration a wrist type blood pressure monitor according to the invention comprises the following steps:
a) The blood pressure of a patient is measured with the wrist type blood pressure monitor to be calibrated.
b) Before or after step a), the blood pressure is measured with an upper arm blood pressure monitor.
c) The blood pressure values obtained in steps a) and b) are compared with each other, e.g. in a calibration device.
d) Depending on the result of the comparison of step c), the wrist type blood pressure monitor is recalibrated, if necessary.

Recalibration is preferably made automatically with the calibration device. It is also conceivable to make a manual recalibration based on values measured with the upper arm blood pressure monitor. In this case, it will be sufficient to enter the correct setting values into the wrist type blood pressure monitor before or after a measurement with the wrist type blood pressure monitor. In this case, it is not necessary to establish a physical connection between the upper armblood pressure monitor and the wrist type blood pressure monitor. The calibration device in this case is contained within the wrist type blood pressure monitor.

In a preferred embodiment of the method, steps a) and b) are repeated, e.g. three times. This enhances accuracy of the measurement and therefore of the calibration.

In a further preferred embodiment, before carrying out step c), it is verified if the blood pressure values measured in steps a) and/or b) are within a predetermined range. The range can be ±20 mmHg for the systolic blood pressure and ±12 mmHg for the diastolic blood pressure.

If the values are not within the predetermined range, steps a) and/or b) may be repeated once more.

In a further preferred embodiment a pause may be made between steps a) and b) and between repetitions of the measurements.

In a further preferred embodiment, the wrist type blood pressure monitor and the upper arm blood pressure monitor are coupled to each other with respective interface connectors before steps a) and b) are carried out. With such a connection, manual entry of data can be dispensed with.

In a further preferred embodiment, the power for the wrist type blood pressure monitor during calibration is supplied by the calibration device. It is necessary to edit the editable memory for calibration. This process can be rather energy consuming. It is therefore preferred, that during calibration, power is not supplied by batteries contained within the wrist type blood pressure monitor but by an external power supply.

The wrist type blood pressuring monitor according the invention is used by the owner in a known manner. If the owner wants to make sure, that his results correlate well with a reference site e.g. the upper arm results, the blood pressure monitor may be recalibrated. For this purpose, a doctor or the vendor of the blood pressure measuring device is provided with a calibrating device. The blood pressure on the upper arm can be measured under the control of a doctor or in a pharmacy. The wrist type blood pressure monitor is thereafter recalibrated. In most general terms, the present invention consists in recalibrating an electronic blood pressure monitor on behalf of blood pressure values determined in a reference measurement and in providing a blood pressure monitor therefore.

Figure 2:
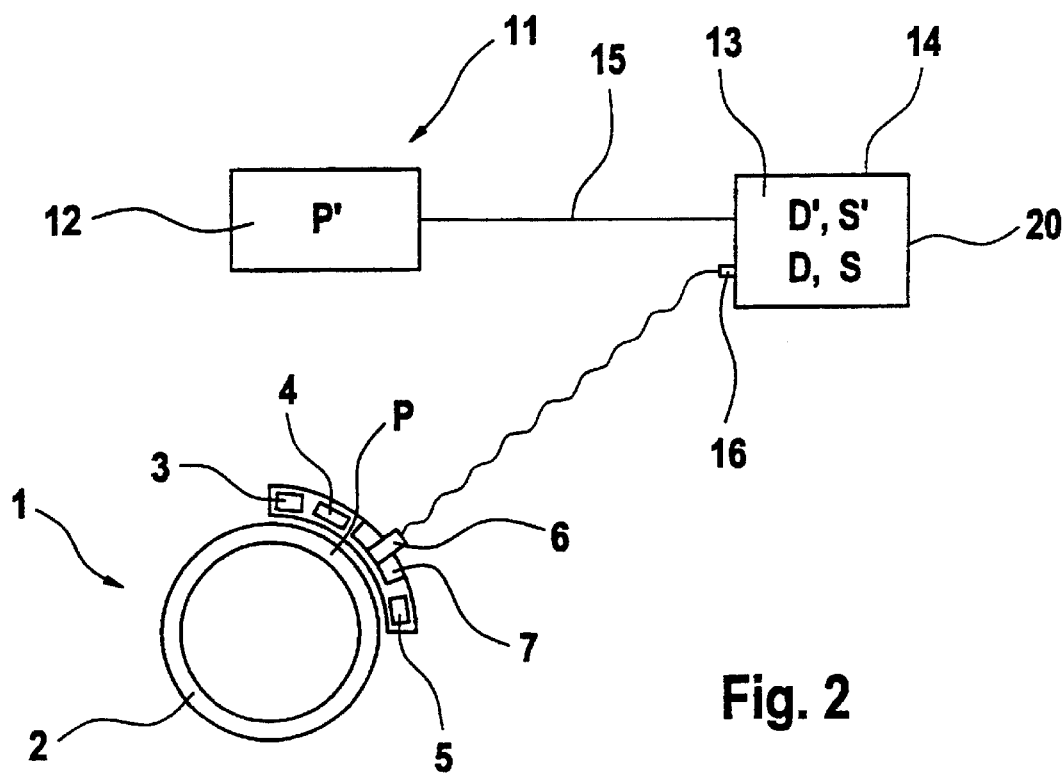
Figure 3:
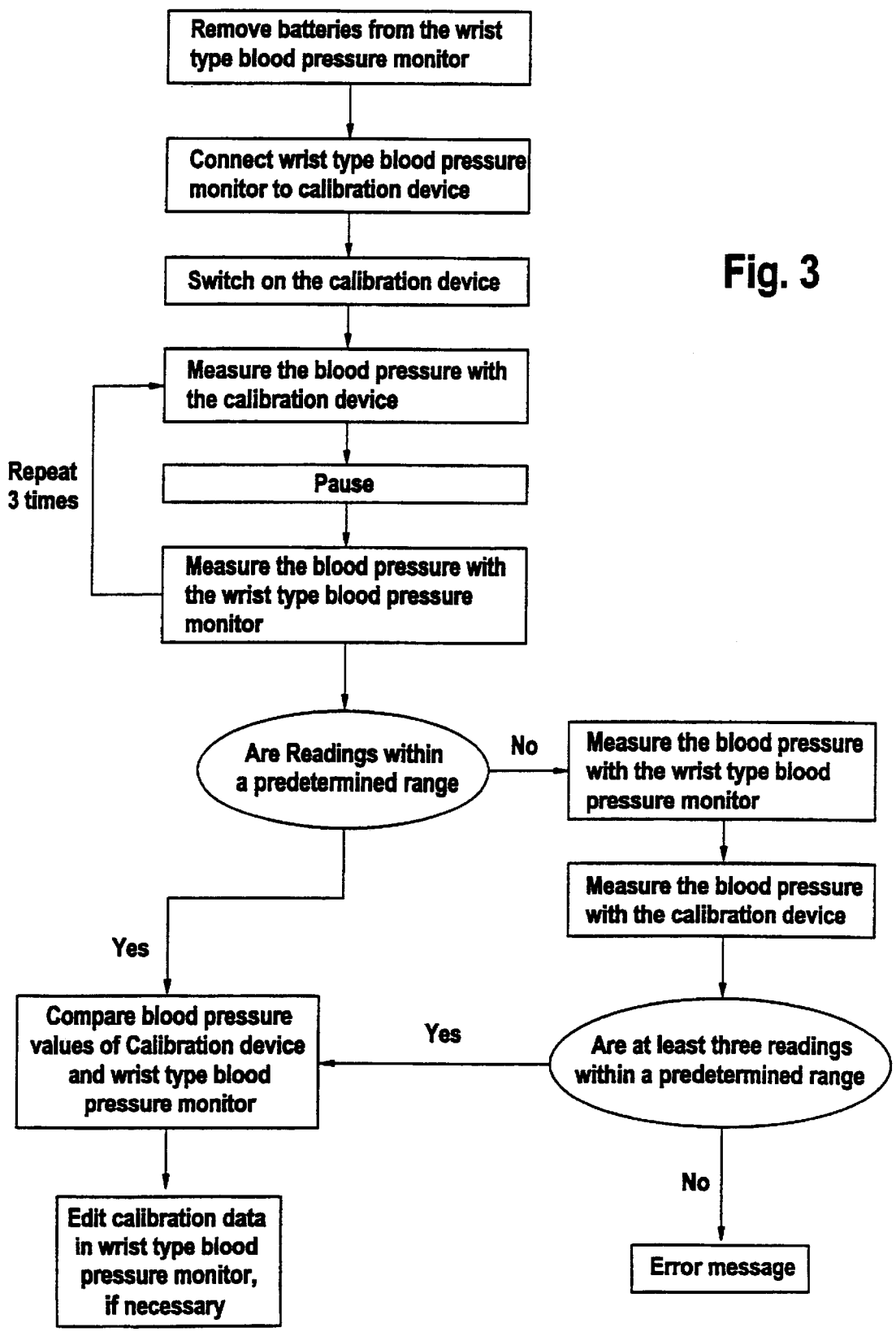

The invention will be more clearly understood on behalf of the following drawings which show:

FIG. 1 a schematic representation of recalibration of a wrist type blood pressure monitor FIG. 2 a schematic representation of a calibration device and a wrist type blood pressure monitor and FIG. 3 a flow chart for the recalibration.

FIG. 1 schematically shows a patient with a wrist type blood pressure monitor 1. The blood pressure is measured based on pressure values measured within a cuff 2 (see FIG. 2) which is placed around the wrist W of the patient.

At about the same time, the blood pressure is also measured with an upper arm blood pressuring monitor 11 with a cuff 12 placed around the upper arm U of the patient.

The wrist type blood pressure monitor 1 is designed in a way known to those skilled in the art and is operating according to the oscillometric method. The blood pressure monitor 1 (see FIG. 2) comprises a cuff 2, a pressure sensor 3 for measuring the blood pressure P within the cuff and calculating arrangement 4 for calculating the blood pressure values, especially the systolic blood pressure S and the diastolic blood pressure D.

The wrist type blood pressure monitor further comprises a memory 5 containing data necessary for calculating the blood pressure values S, D. The memory 5 especially carries data for calibrating the measurement results.

The wrist type blood pressure monitor 1 further comprises an interface connector 6. Interface connector 6 allows connection between the wrist type blood pressure monitor 1 and a calibrating device 20.

In FIG. 1 or 2, a wire connection is shown. Wireless communication is also conceivable.

The calibrating device 20 comprises a calculating arrangement 14 for calculating the blood pressure values D', S' based on the pressure P' measured within the cuff 12 placed around the upper arm U of the patient. The calibration device 20 comprises an interface connector 16 which allows connection with the wrist type blood pressure monitor 1. The calibration device is further provided with a power supply 21 which can also be used to supply the wrist type blood pressure monitor 1 with electricity during the calibration process.

The upper arm blood pressure monitor 11 is designed in a manner known to those skilled in the art. It especially comprises a cuff 12 connected via a tube 15 to the calibration device 20.

Within the calibration device 20, a usual calculating arrangement 14 and pressure sensor 13 are arranged.

In FIG. 3, a flow chart for the calibration process is shown. In a first step, the batteries are removed from the wrist type blood pressure monitor 1. This is necessary for establishing a connection with the interface connector 6 which is arranged within the battery compartment 5.

The wrist type blood pressure monitor is then connected to the calibration device 20.

Subsequently, the calibration device is switched on. The wrist type blood pressure monitor 1 is thereafter controlled through the calibration device 20.

The blood pressure is then measured with the calibration device 20 (i.e. based on the upper arm cuff 12) and with the wrist type blood pressure monitor 1. These measurements are repeated for e.g. three times. Each measurement lasts about for sixty seconds. A pause of sixty seconds is made between to subsequent measurements.

Subsequently, it is determined if the results of the measurements are within a predetermined range. The range is typically ±20 mmHg for the systolic and ±12 mmHg for the diastolic blood pressure.

If the readings are not within the predetermined range, the measurement with the wrist type blood pressure monitor and/or with the calibration device are repeated. Based on the four-measurements, it is determined if at least three readings are within the predetermined range. If this is still not the case, an error message is given.

If after three or four measurements, the readings are within the predetermined range, the blood pressure values D, S given by the wrist type blood pressure monitor 1 and the values D',S' given by the calibration device 20 are compared to each other. Based on possible differences between the values D and D' and S and S', the calibration data in the memory 5 are amended according to a specific algorithm.

After writing the corrected calibration values into the memory 5, a message indicating successful calibration may be given and both, the wrist type blood pressure monitor 1 and the calibration device 20 are switched off.

The memory 5 is an EEPROM. The calibration device writes the new defined constants into the EEPROM of the monitor.

There is a factory setting (factory calibration constants for the "average patient") stored in the masked IC (single chip microprocessor). After starting the program it first checks if there is any calibration constant stored in the EEPROM. If there is no value in the EEPROM, the program will use the factory setting of the microprocessor. If there is a value (systolic and diastolic calibration constants) in the EEPROM, the microprocessor will use the new constants for the EEPROM for evaluation of the patient's systolic and diastolic blood pressure values.

The wrist type blood pressure monitor 1 further may comprise means for resetting the calibration to the factory values. It is also conceivable to provide one and the same wrist type blood pressure monitor 1 with several calibration sets which may be valid for several users.

A wrist type blood pressure monitor 1 which is designed for use by one single patient may further be provided with a label indicating the name of the user. The label may also be electronic.

What is claimed is:

1. A self-contained wrist-type blood pressure monitor comprising:
   (i) an inflatable cuff adapted to be placed around the wrist of a patient;
   (ii) a pressure sensor for measuring the pressure within said cuff;
   (iii) a calculating arrangement for calculating diastolic and systolic blood pressure values based on pressure values measured within said cuff, which has an editable memory provided with calibration data such as calibration data to be used in the calculation process of the calculation arrangement;
   (iv) an interface connector being connectable to the interface connector of a calibrating device for calibration of the wrist type blood pressure monitor, whereby calibration data provided by the calibration device is storable in the editable memory of the calculation arrangement.

2. A self-contained wrist-type blood pressure monitor according to claim 1, wherein the blood pressure monitor has a battery compartment and wherein said interface connector is arranged within or next to said battery compartment.

3. A self-contained wrist-type blood pressure monitor according to claim 2, wherein said interface connector is adapted to be connected to an external power supply during calibration.

4. A self-contained wrist-type blood pressure monitor according to claim 1, wherein the editable memory is an EEPROM.

5. A system for calibrating a wrist type blood pressure monitor, system comprising:
   (a) a self-contained wrist type blood pressure monitor adapted to measure the diastolic and systolic blood pressure of a patient, said monitor having
      (i) an inflatable cuff adapted to be placed around the wrist of a patient;
      (ii) a pressure sensor for measuring the pressure within said cuff;
      (iii) a calculating arrangement for calculating diastolic and systolic blood pressure values based on pressure values measured within said cuff, said calculating arrangement having an editable memory;
      (iv) an interface connector;
   (b) a calibration device for calibrating the wrist type blood pressure monitor, said calibration device having
      (i) an inflatable cuff adapted to be placed around the upper arm of a patient;
      (ii) a pressure sensor for measuring the pressure within said cuff;
      (iii) a calculating arrangement for calculating blood pressure values based on pressure values measured within said cuff, having an interface connector;
   the interface connector of the wrist type blood pressure monitor being connectable to the interface connector of the calibrating device for calibration of the wrist type blood pressure monitor, whereby calibration data provided by the calibration device is storable in the editable memory of the wrist type blood pressure monitor.

6. A system according to claim 5, whereby the calibration device provides power supply for the wrist type blood pressure monitor during calibration.

7. A system according to claim 6, wherein the wrist type blood pressure monitor has a battery compartment and wherein the interface connector is arranged within or next to said battery compartment.

8. A system according to claim 5, wherein the editable memory of the wrist type blood pressure monitor is an EEPROM.

9. A method for calibrating a self-contained wrist type blood pressure monitor having an inflatable cuff adapted to be placed around the wrist of a patient and to determine the diastolic and the systolic blood pressure of the patient, said method comprising the steps of:
   a) measuring the patient's blood pressure with the wrist type blood pressure monitor to be calibrated;
   b) before or after step a), coupling the wrist type blood pressure monitor and an upper arm blood pressure monitor together via respective interface connectors;
   c) measuring the blood pressure with the upper arm pressure monitor;
   d) comparing the blood pressure values obtained in steps a) and b);
   e) depending on the results of step d), recalibrating the wrist type blood pressure monitor, if necessary; and
   f) after step c), d) or e), uncoupling the wrist type blood pressure monitor from the upper arm blood pressure monitor.

10. A method according to claim 9, wherein steps a) and c) are repeated, preferably three times, before step d).

11. A method according to claim 9, comprising a further step of, before carrying out step d), verifying that the blood pressure values measured in steps a) and/or c) are within a predetermined range.

12. A method according to claim 11, wherein steps a) and/or c) are repeated once more if the values of the blood pressure are not within the predetermined range.

13. A method according to claim 9, wherein a pause is made between steps a) and c) or between subsequent repetitions of steps a) and c).

14. A method according to claim 9, wherein during calibration, power for the wrist type blood pressure monitor is supplied by the calibration device.

* * * * *